United States Patent
Aferzon et al.

(10) Patent No.: US 7,594,932 B2
(45) Date of Patent: Sep. 29, 2009

(54) APPARATUS FOR ANTERIOR INTERVERTEBRAL SPINAL FIXATION AND FUSION

(75) Inventors: Joseph Aferzon, Avon, CT (US); Joshua Michael Aferzon, Avon, CT (US)

(73) Assignee: International Spinal Innovations, LLC, West Hartford, CT (US)

( * ) Notice: Subject to any disclaimer, the term of this patent is extended or adjusted under 35 U.S.C. 154(b) by 413 days.

(21) Appl. No.: 11/321,936

(22) Filed: Dec. 29, 2005

(65) Prior Publication Data

US 2008/0132949 A1 Jun. 5, 2008

(51) Int. Cl.
*A61F 2/44* (2006.01)
(52) U.S. Cl. .................................... 623/17.16
(58) Field of Classification Search ... 623/17.11–17.16; 83/665; 30/169
See application file for complete search history.

(56) References Cited

U.S. PATENT DOCUMENTS

| | | | | |
|---|---|---|---|---|
| 1,217,326 | A * | 2/1917 | Meinecke | 83/665 |
| 2,815,077 | A * | 12/1957 | Pechy | 83/430 |
| 2,864,421 | A * | 12/1958 | Schmidt | 83/665 |
| 5,254,118 | A | 10/1993 | Mirkovic | |
| 5,522,441 | A * | 6/1996 | Anselm et al. | 142/41 |
| 5,683,394 | A * | 11/1997 | Rinner | 606/86 R |
| 6,012,372 | A * | 1/2000 | Laster et al. | 83/665 |
| 6,159,211 | A * | 12/2000 | Boriani et al. | 606/279 |
| 6,227,093 | B1 * | 5/2001 | Rensky, Jr. | 83/563 |
| 6,241,769 | B1 * | 6/2001 | Nicholson et al. | 623/17.11 |
| 6,302,914 | B1 * | 10/2001 | Michelson | 623/17.16 |
| 6,443,990 | B1 * | 9/2002 | Aebi et al. | 623/17.16 |
| 6,447,544 | B1 * | 9/2002 | Michelson | 623/17.16 |
| 6,447,547 | B1 * | 9/2002 | Michelson | 623/17.16 |
| 6,527,803 | B1 * | 3/2003 | Crozet et al. | 623/17.11 |
| 6,558,424 | B2 * | 5/2003 | Thalgott | 623/17.16 |
| 6,767,367 | B1 * | 7/2004 | Michelson | 623/17.16 |
| 6,770,096 | B2 * | 8/2004 | Bolger et al. | 623/17.16 |
| 6,824,564 | B2 * | 11/2004 | Crozet | 623/17.11 |
| 6,923,830 | B2 * | 8/2005 | Michelson | 623/17.16 |
| 7,056,341 | B2 * | 6/2006 | Crozet | 623/17.11 |
| 7,238,203 | B2 * | 7/2007 | Bagga et al. | 623/17.11 |
| 2002/0143401 | A1 * | 10/2002 | Michelson | 623/17.16 |
| 2003/0004576 | A1 * | 1/2003 | Thalgott | 623/17.16 |
| 2003/0187436 | A1 * | 10/2003 | Bolger et al. | 606/61 |
| 2004/0138752 | A1 * | 7/2004 | Michelson | 623/17.11 |
| 2005/0143825 | A1 * | 6/2005 | Enayati | 623/17.16 |
| 2007/0055376 | A1 * | 3/2007 | Michelson | 623/17.11 |
| 2007/0270968 | A1 * | 11/2007 | Baynham et al. | 623/17.11 |
| 2008/0255666 | A1 * | 10/2008 | Fisher et al. | 623/17.16 |

* cited by examiner

*Primary Examiner*—Eduardo C Robert
*Assistant Examiner*—Ellen Rust
(74) *Attorney, Agent, or Firm*—Hoffmann & Baron. LLP

(57) ABSTRACT

A spinal fixation and fusion device that includes a housing with leading deep surface conforming to the posterior aspect of the intervertebral disk and trailing outer surface conforming to the anterior surface of the disk, weight bearing sides and the top and bottom surfaces with plurality of openings enabling ingrowths of bone. The device further includes a shaft running from the center of the deep surface and perpendicular to the deep surface of the housing to the center of the outer surface of the housing and affixed at least to the deep surface of the housing, and a flat metal member threaded onto the shaft with sharp leading edge which upon clockwise or counterclockwise rotation about the axis of the shaft will break the endplate, hook into the vertebra and rigidly secure the vertebra to the entire device preventing separation of the vertebra from the device during spinal motion.

17 Claims, 18 Drawing Sheets

US 7,594,932 B2

APPARATUS FOR ANTERIOR INTERVERTEBRAL SPINAL FIXATION AND FUSION

FIELD OF INVENTION

This invention relates to a spinal fusion device. More specifically, the present invention relates to an implant and fixation device used to reconstruct a spinal disk space and facilitate fusion across the spinal disk space.

BACKGROUND

Articulations between bony vertebras of a human spine frequently deteriorate with age or trauma and become a source of pain. A spinal disk is one of these articulations and with the aging process it loses its normal consistency and volume and collapses allowing for abnormally painful motion within the anterior spinal column. The spinal disk is a complex cylindrical weigh-bearing fibrous structure with a non-compressible viscous center. The spinal disk articulates with a bony vertebra above and below through a large surface area circular interface known as an endplate (FIG. 1). The endplate is a thin (1-3 mm) approximately round 2-4 cm in diameter plate of dense bone and cartilage accounting for majority of the vertebral weight-bearing capacity (FIG. 2).

Surgical treatment of disk disorders frequently requires elimination of movement across an abnormal spinal disk. This is accomplished by allowing bone to grow between adjacent vertebra and through a disk space of the abnormal spinal disk. It is desirable to reconstruct the disk space to its prior normal height by opening the space previously occupied by the removed spinal disk while retaining normal curvature of the spine determined by the differential height between the front and the back of the spinal disk (FIG. 3). This is commonly achieved by using inserts or implants, which open the disk space and which allow for growth of bridging bone. The ultimate effectiveness of an implant is based on the following factors: (i) ability to reconstruct and maintain a normal configuration of a vertebral column; (ii) ease of insertion; (iii) facilitation of bony fusion; and (iv) restriction of movement across the disk space.

Implants utilized in fusion of a human spine and delivered in a straight trajectory through the front of the spine and into the disk space are well known to those skilled in the art. They vary in shape but possess similar characteristics with upper and lower surfaces conforming to a shape of vertebral endplates and a vertical design aiming to open or reconstruct the collapsed disk space. These implants are sufficiently porous or hollow to allow bone to grow through the implants and bridge two vertebras referred to as bone fusion. These implants perform well with vertical loading of the spine or in flexion. However, these implants are not able to restrict the movement between two vertebras when vertebras are pulled apart or are in extension and lateral bending. Further, these implants provide negligible restriction during sliding motion (translation) and rotation.

Devices that cut into or have protrusions directed into or through the endplate, are also known in the related art. These protrusions penetrate the endplate and potentially create channels for a bone growth, yet the protrusions do not alter structural properties of the endplate. The protrusions also reduce the risk of extrusion of the implant out of the disk space. These protrusions negligibly restrict translation or sliding motion but they do not restrict extension and lateral bending. This necessitates additional fixation (immobilization) usually consisting of posterior pedicle screws.

There would be a substantial benefit in an anterior fixation device which would on its own rigidly fixate the spine in all direction of motion.

SUMMARY OF THE INVENTION

A device utilized in reconstruction and fusion of a human spine providing direct rigid fixation of an anterior spinal column in flexion, extension and rotation. The device includes a housing with a leading deep surface conforming to a posterior aspect of an intervertebral disk and a trailing outer surface conforming to an anterior surface of the intervertebral disk, weight bearing sides and top and bottom surfaces with a plurality of openings enabling ingrowths of bone. The device further includes a shaft running from a center of the leading deep surface and perpendicular to the leading deep surface of the housing to the center of the trailing outer surface of the housing, the shaft being affixed at least to the leading deep surface of the housing. The device also includes at least one flat metal member threaded onto the shaft with a sharp leading edge which upon clockwise or counterclockwise rotation about the axis of the shaft will break an endplate, hook into a vertebra and rigidly secure the vertebra to the entire device preventing separation of the vertebra from the device during spinal motion.

DETAILED DESCRIPTION

An implant device for reconstruction, fixation and bone fusion of bone vertebras through an anterior approach to the human spine. This implant device enables rigid fixation in all planes of motion including extension of the spine, it possesses structural characteristics necessary to reconstruct and maintain disk height, it provides space for bone grafting material and produces a plurality of perforations through endplates above and below to enhance bony fusion.

The implant device consists of the outer structure or shell which is designed to conform to the disk space, provide openings for bony ingrowths and maintain the disk height by providing adequate structural strength and sufficient weight bearing surface. The shell or housing contains a shaft, which runs through its central axis from the back to the front and is fixed to the shell at its back (FIG. 7).

Figure 12:
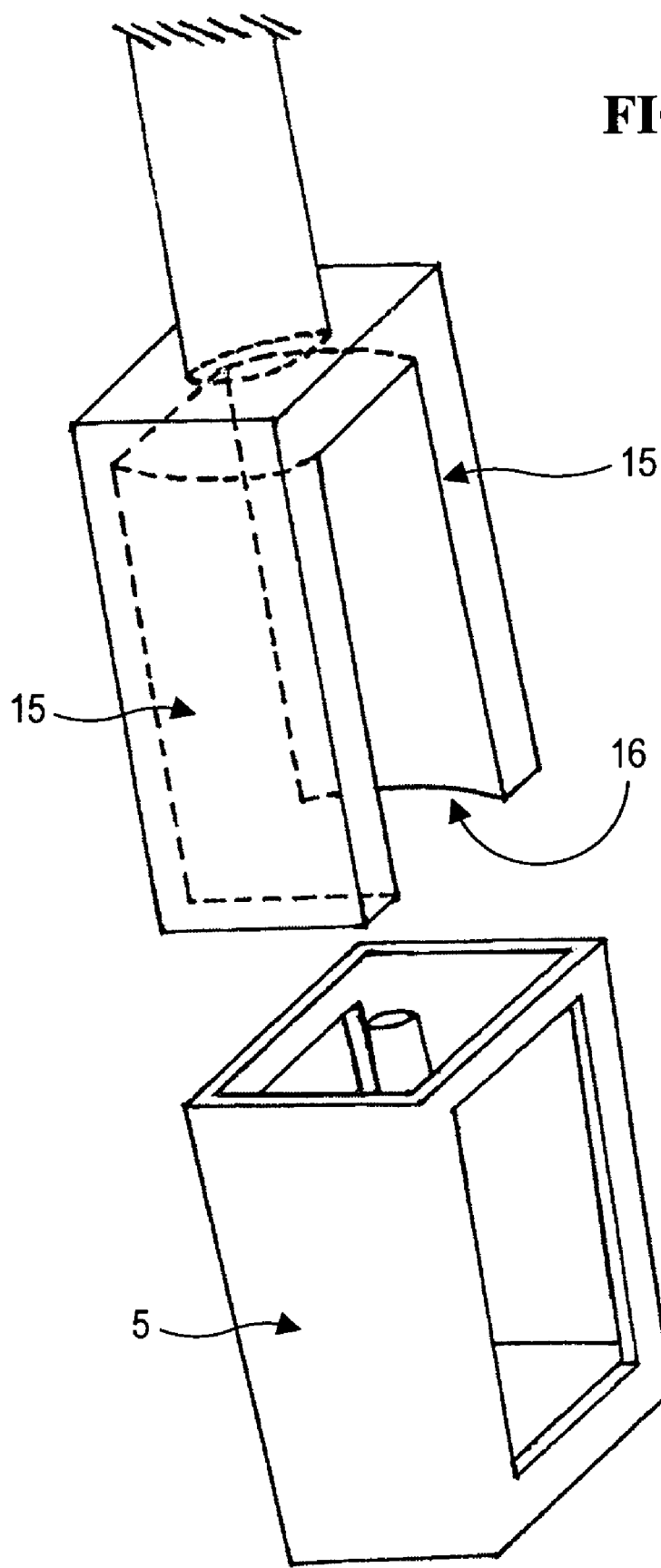
FIG. 12 Preferred embodiment of the insertion instrument for the housing. The prongs (15) fit inside the lateral walls (5) of the housing but clear the central opening (16) occupied by the blades.
Figure 13:
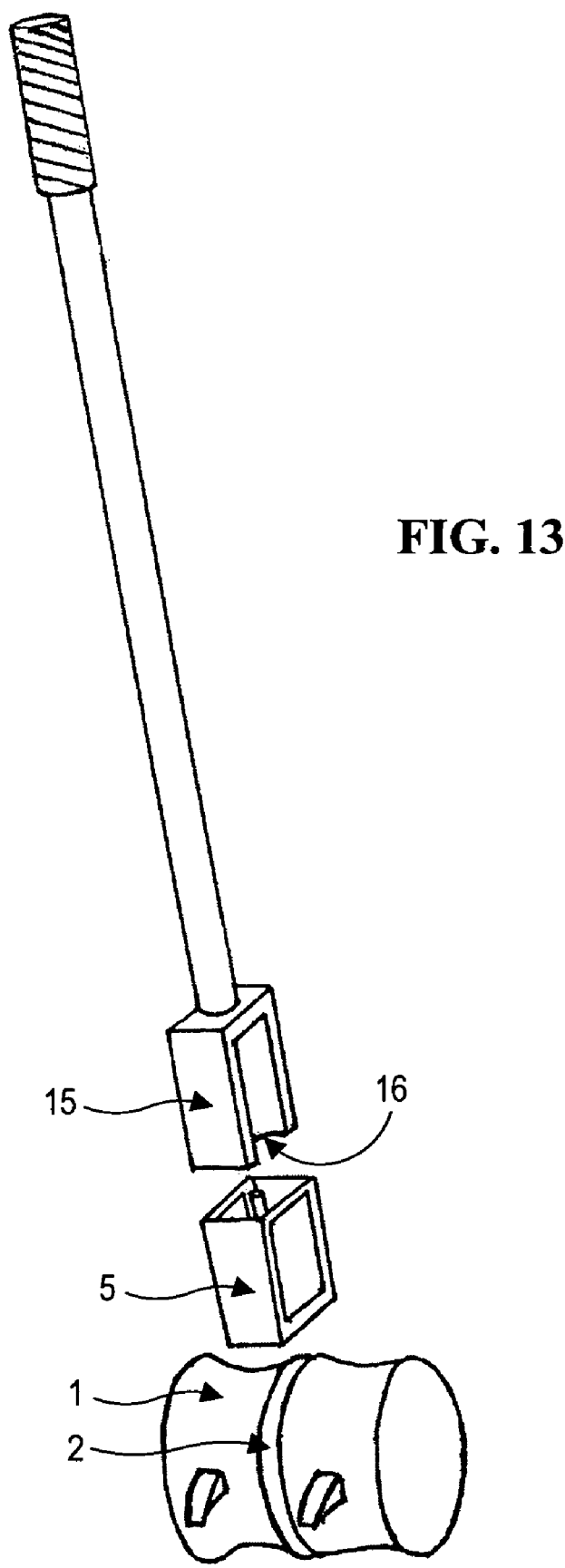
FIG. 13 Preferred method of housing placement into collapsed disk space (2) between vertebras (1).
Figure 14:
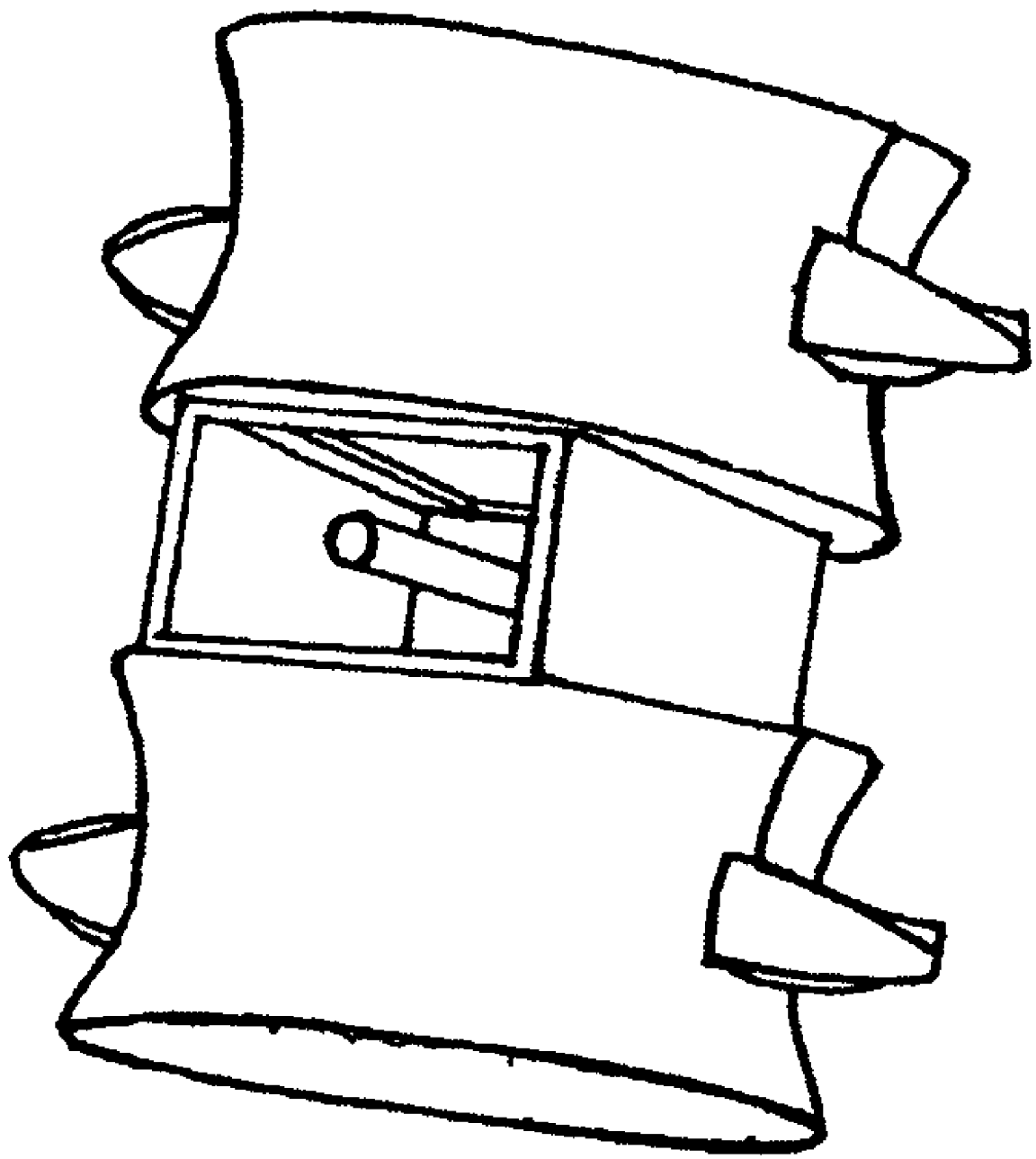
FIG. 14 Housing inside expanded disk space (2).

In the preferred embodiment the shell is impacted into the disk space (FIG. 14) using the shell introducer (FIG. 13). The shell introducer fits tightly to the sides of the shell but is open in the center to allow for blades (FIG. 12).

Figure 11:
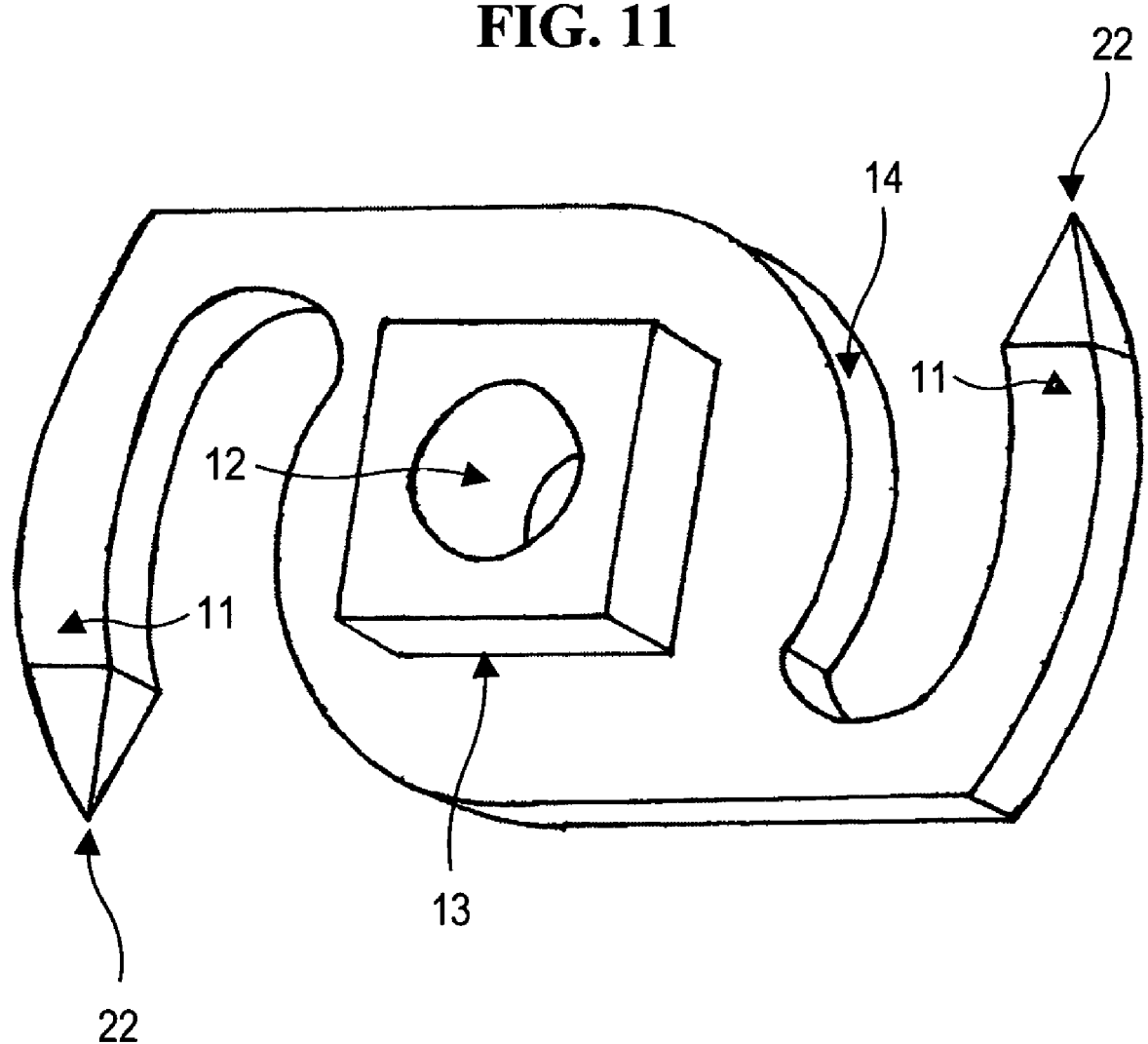
FIG. 11 Perspective view of the counterclockwise blade
Figure 15:
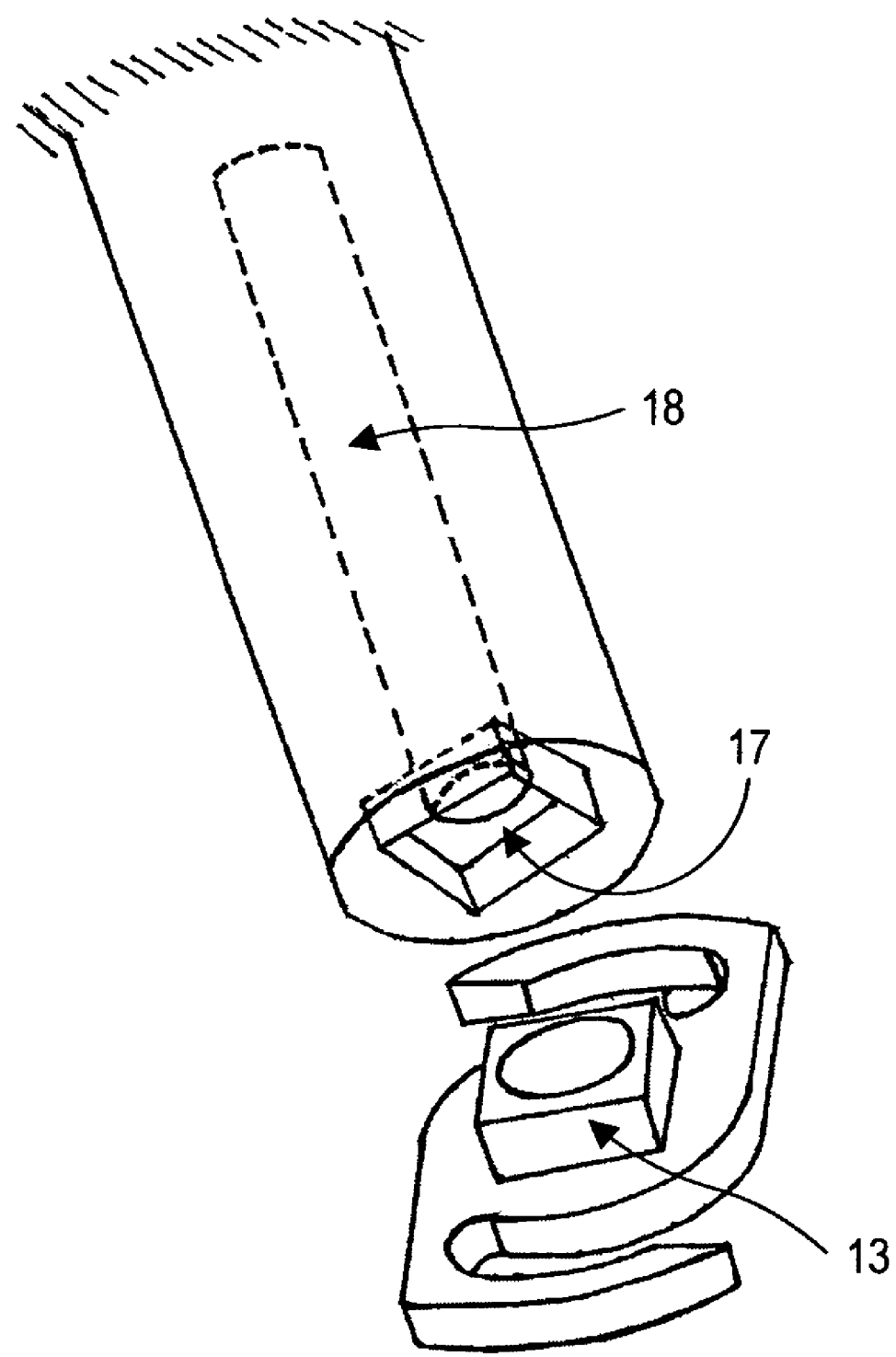
FIG. 15 Preferred embodiment of a blade introducer having a receptacle (17) for the control nut (13) and a central opening (18) for the shaft (10).
Figure 16:
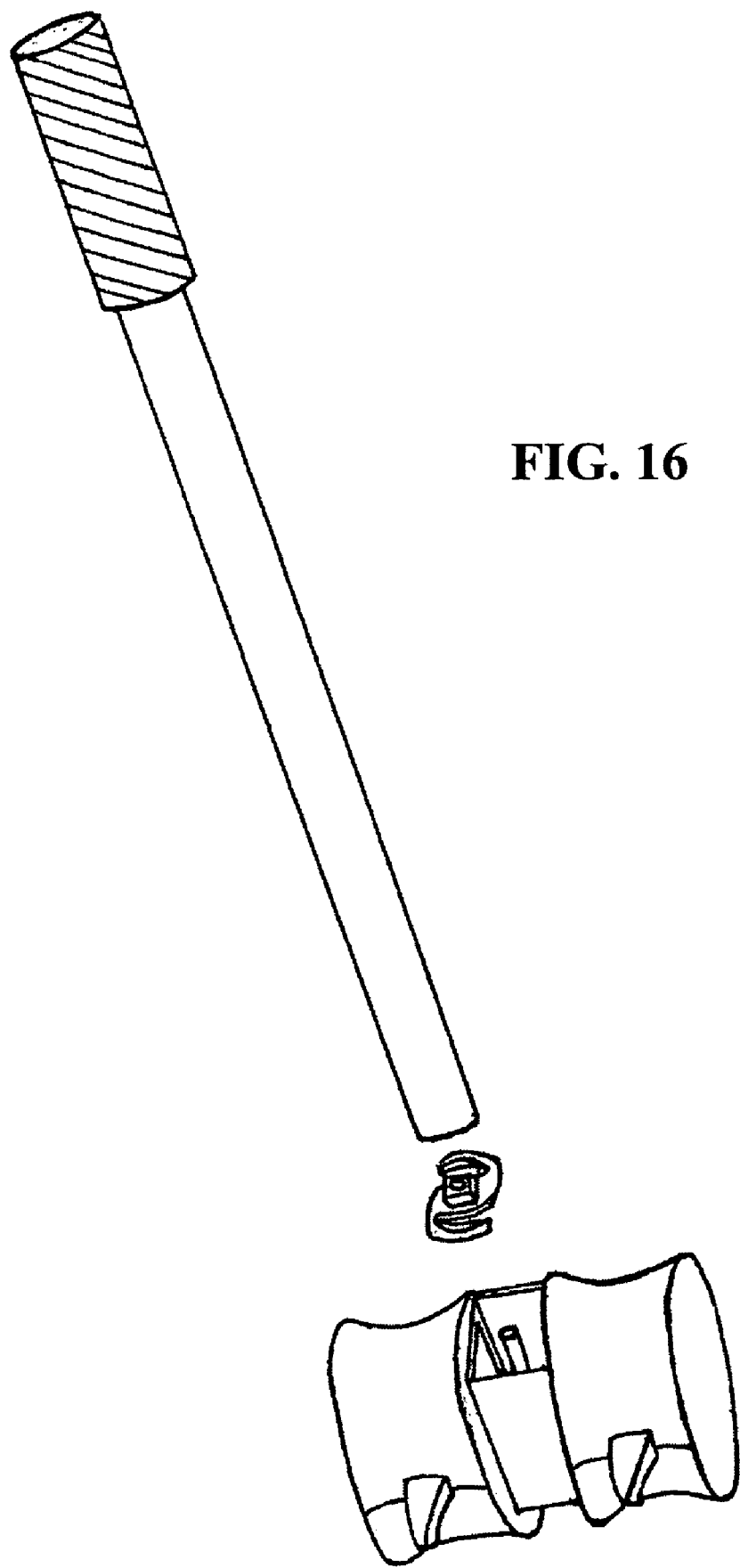
FIG. 16 Blade of FIG. 8 introduced horizontally into the housing of FIG. 7 using the blade introducer of FIG. 15.
Figure 17:
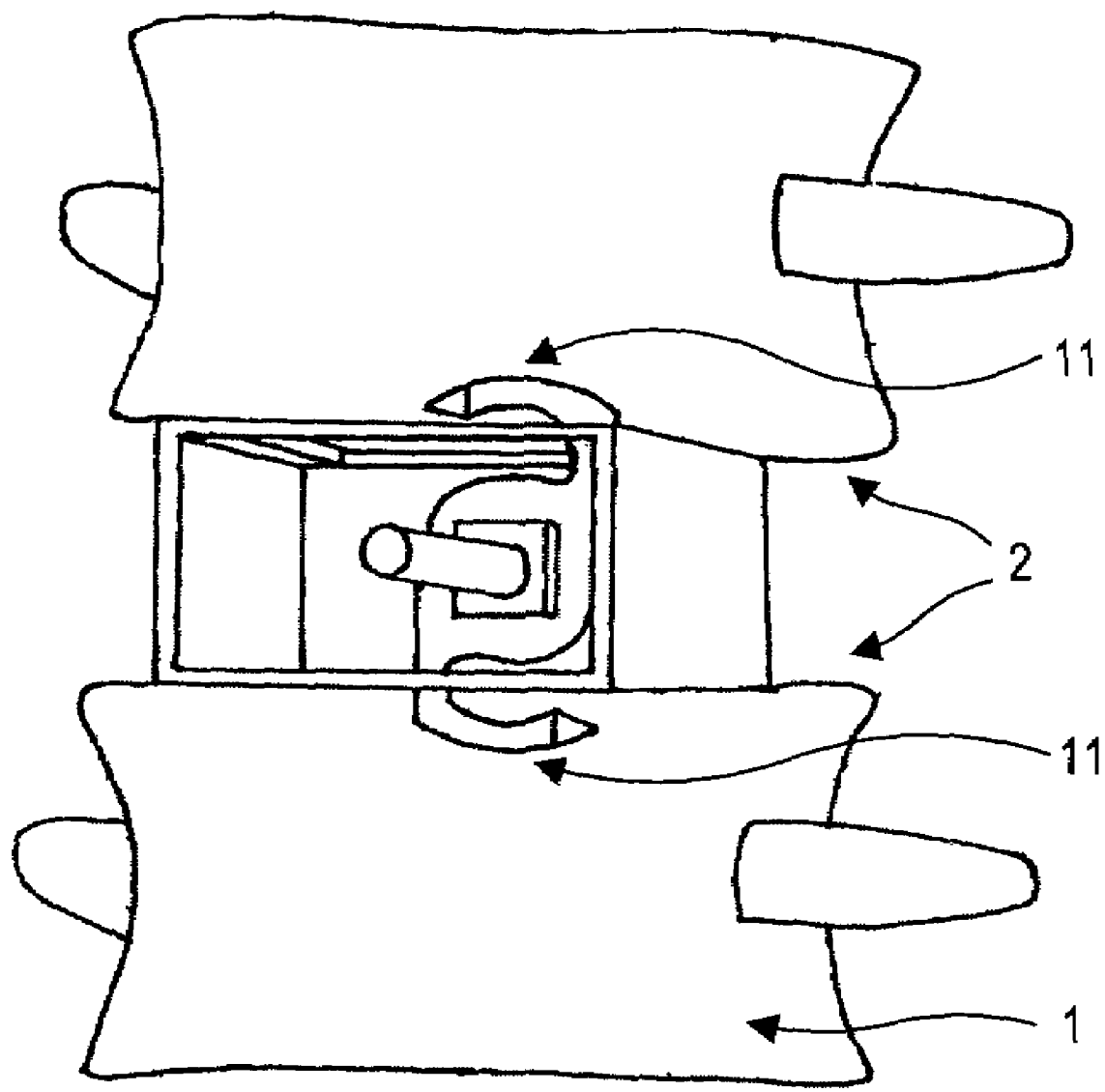
FIG. 17 Blade rotated vertically with cutting extensions (11) piercing vertebral endplates and hooking into vertebras (1).

Once the shell is placed in a correct position, individual blades (FIG. 11) are selected, mounted onto the introducer (FIG. 15) and threaded onto the shaft in horizontal orientation (FIG. 16). The blade is placed as deep as it can go and then rotated into vertical orientation breaking the endplate and hooking into the vertebra (FIG. 17). The blades alternate between clockwise and counterclockwise orientation. Variable size blades can be selected to better approximate the configuration of the disk space.

Figure 1:
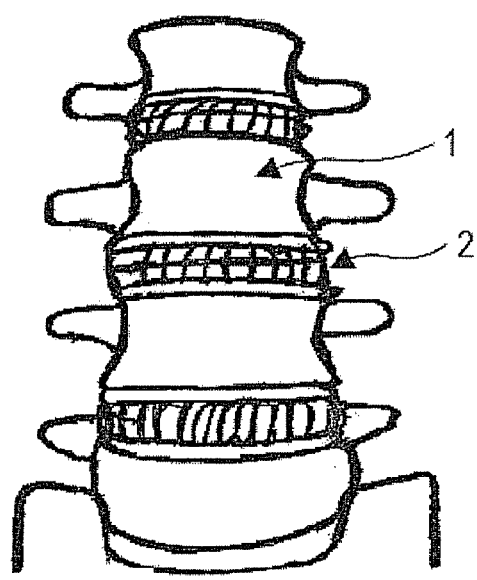
FIG. 1 Anterior view of the lumbar spine demonstrating vertebra (1) alternating with disk (2).
Figure 2:
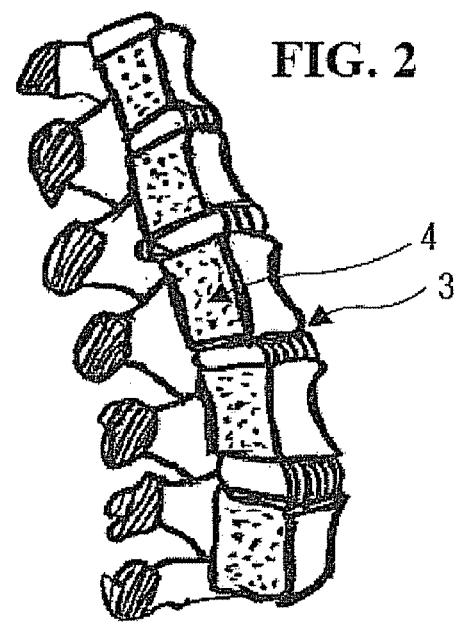
FIG. 2 Anterior view of the vertically sliced lumbar spine demonstrating internal composition of the vertebra with dense endplate (3) and softer inner part (4).
Figure 3:
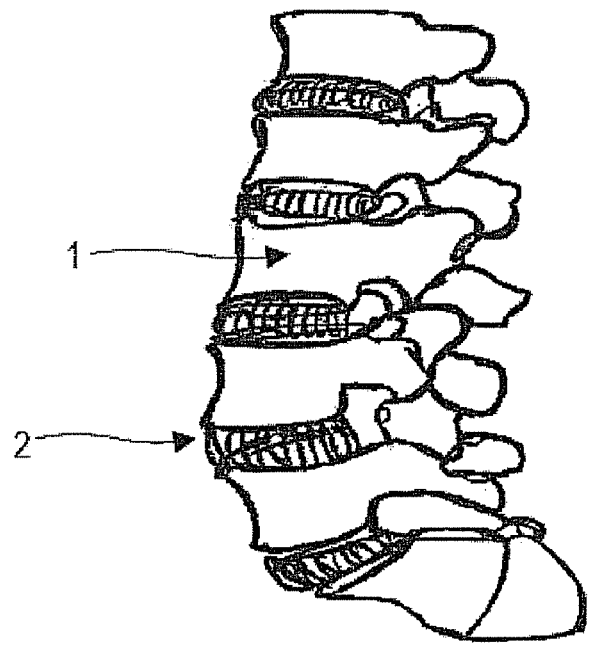
FIG. 3 Lateral (side) view of the vertebral column demonstrating normal curvature (lordosis) of the lumbar spine.
Figure 4:
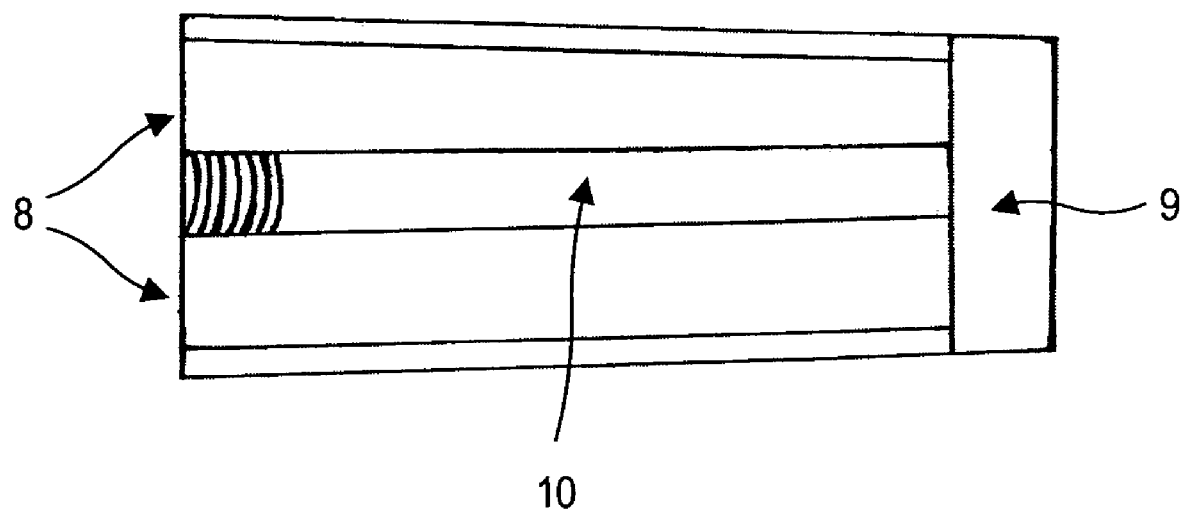
FIG. 4 Lateral (side) view of the preferred embodiment of the housing with front opening (8), back wall (9), and a central shaft (10) fixed to the back wall (9).
Figure 5:
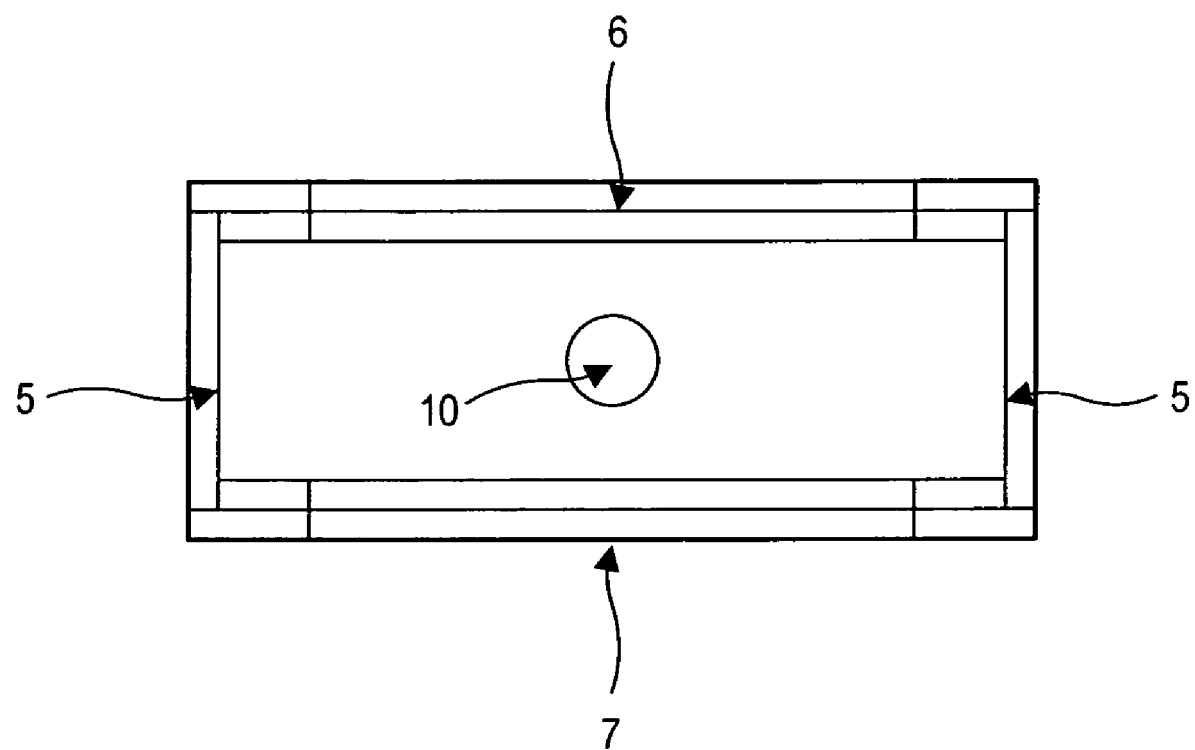
FIG. 5 Anterior (front) view through the front opening (8) of the housing with lateral weight bearing walls (5), top (6) and bottom (7) openings, and the central shaft (10).
Figure 6:
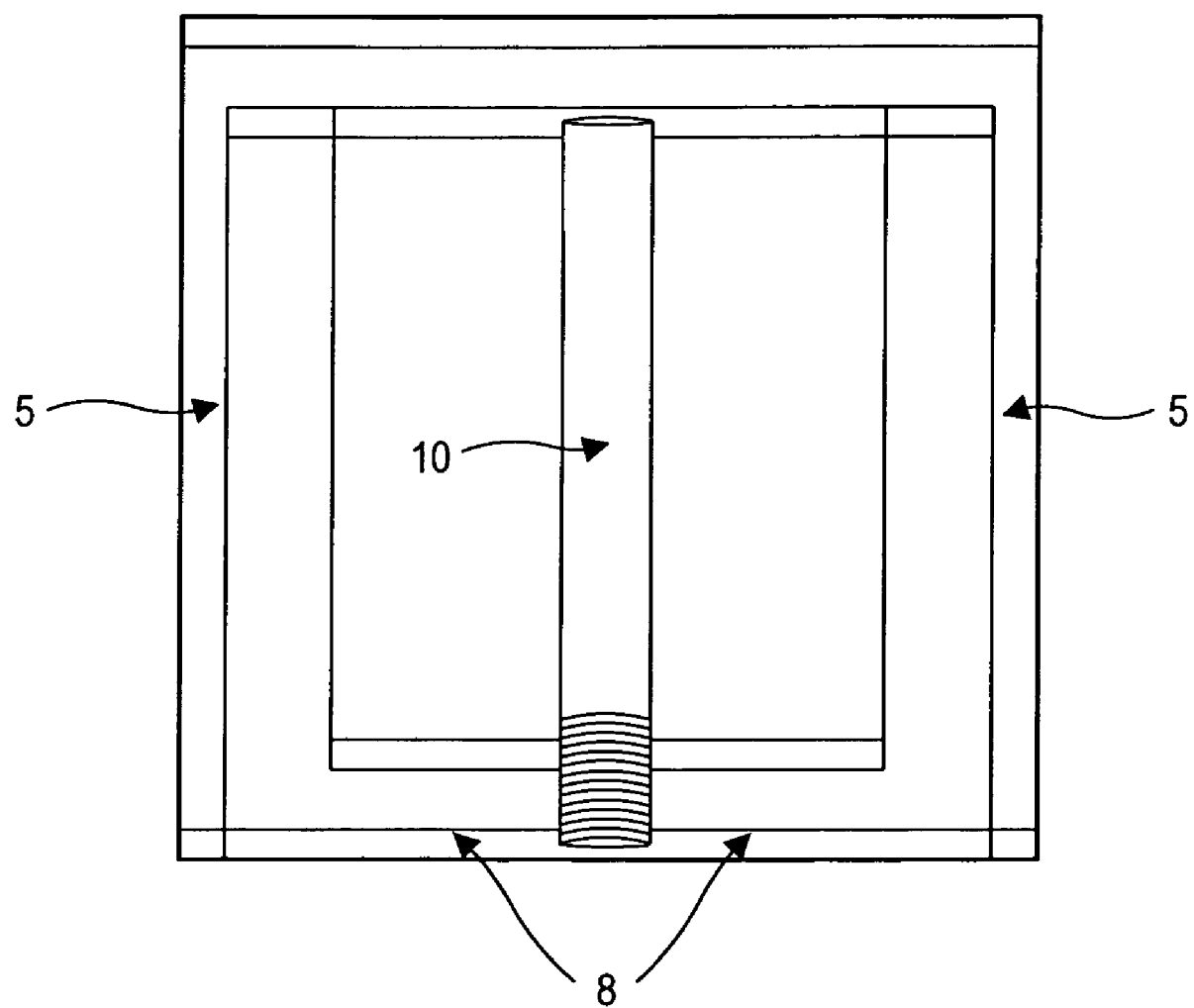
FIG. 6 Superior (top) view through the top opening (6) of the housing, showing the central shaft (10).
Figure 7:
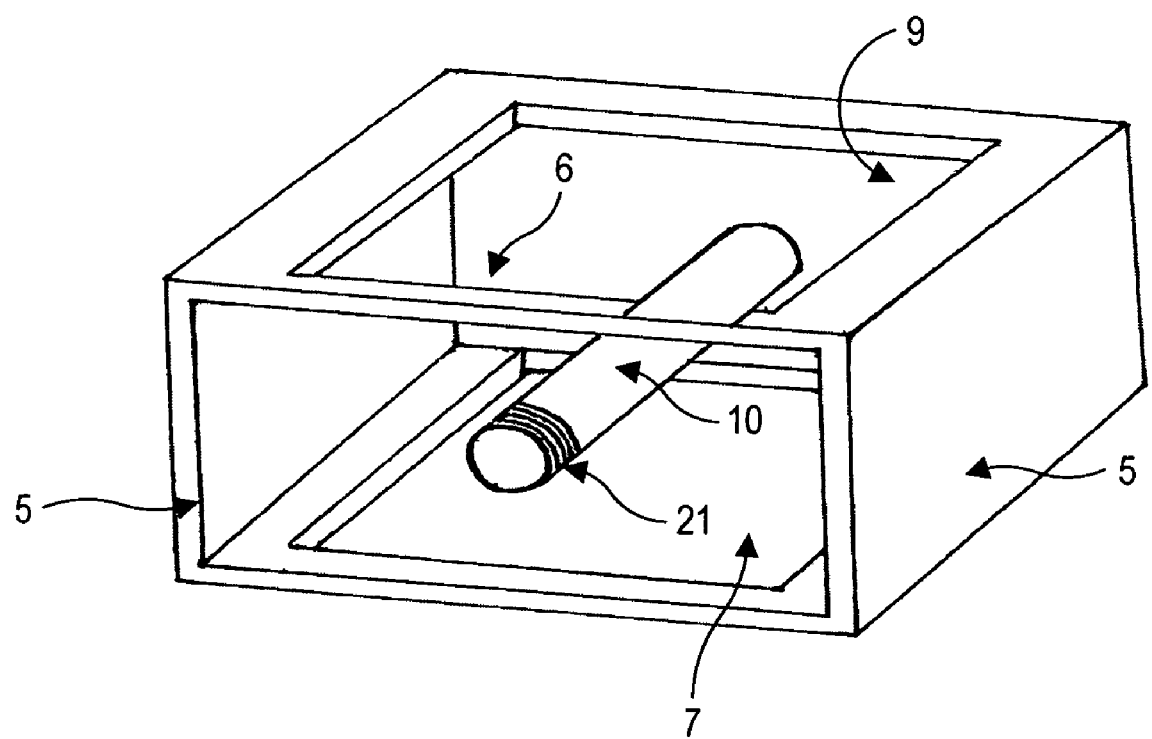
FIG. 7 Perspective view of the housing with lateral weight bearing walls (5), top (6) and bottom (7) openings, back wall (9), and a central shaft (10) including threaded end (21).
Figure 8:
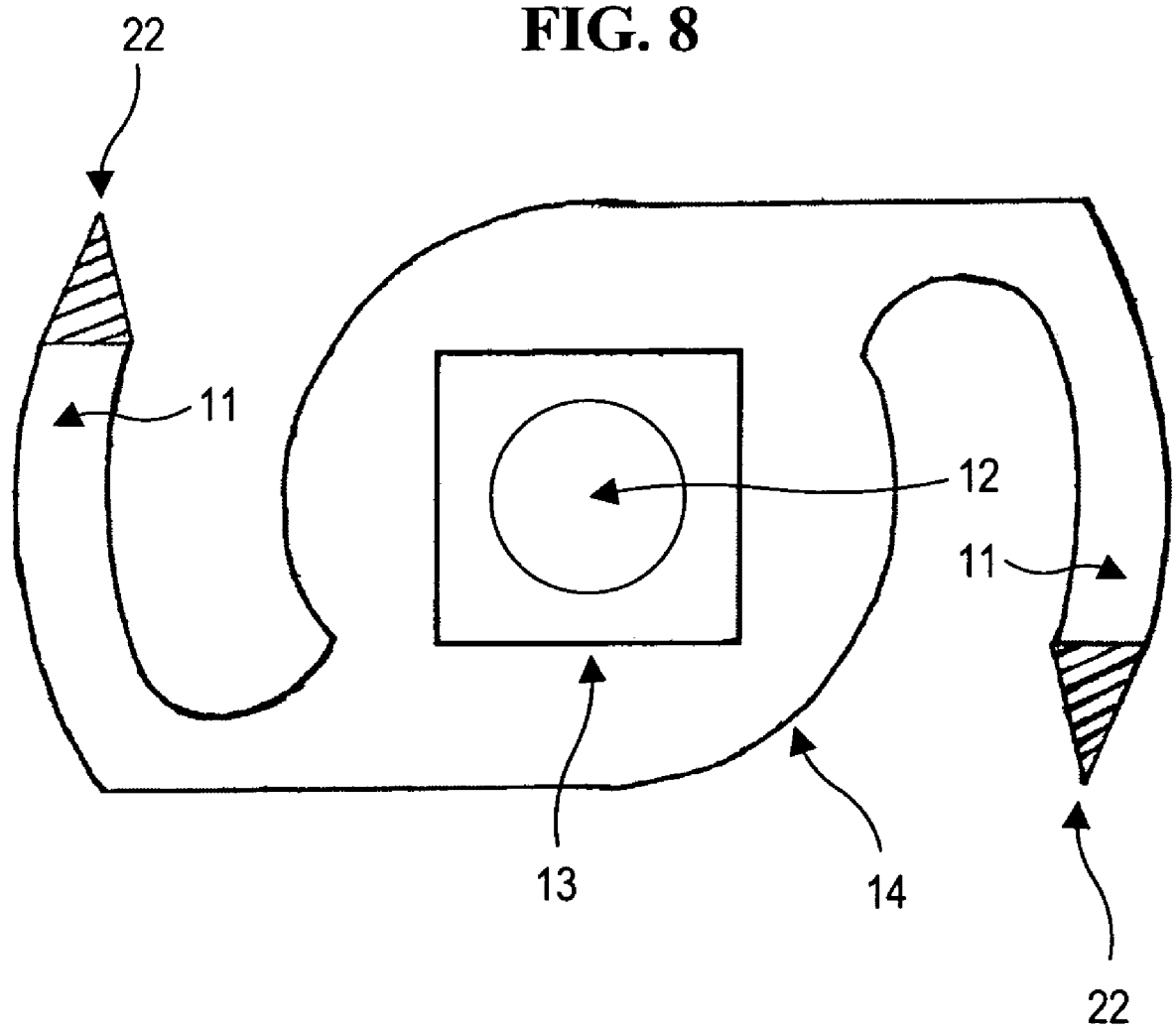
FIG. 8 Front view of the preferred embodiment of the clockwise blade. The cuffing extensions (11) have sharp ends (22) that cut through the endplate 3 and into the cancellous bone (4) of vertebra (1). The central opening (12) fits over the shaft 10 of the housing. The control nut (13) is used to handle the blade and to thread onto the shaft (10). The body of the blade (14) provides additional central weight bearing support against vertebral endplates.
Figure 9:
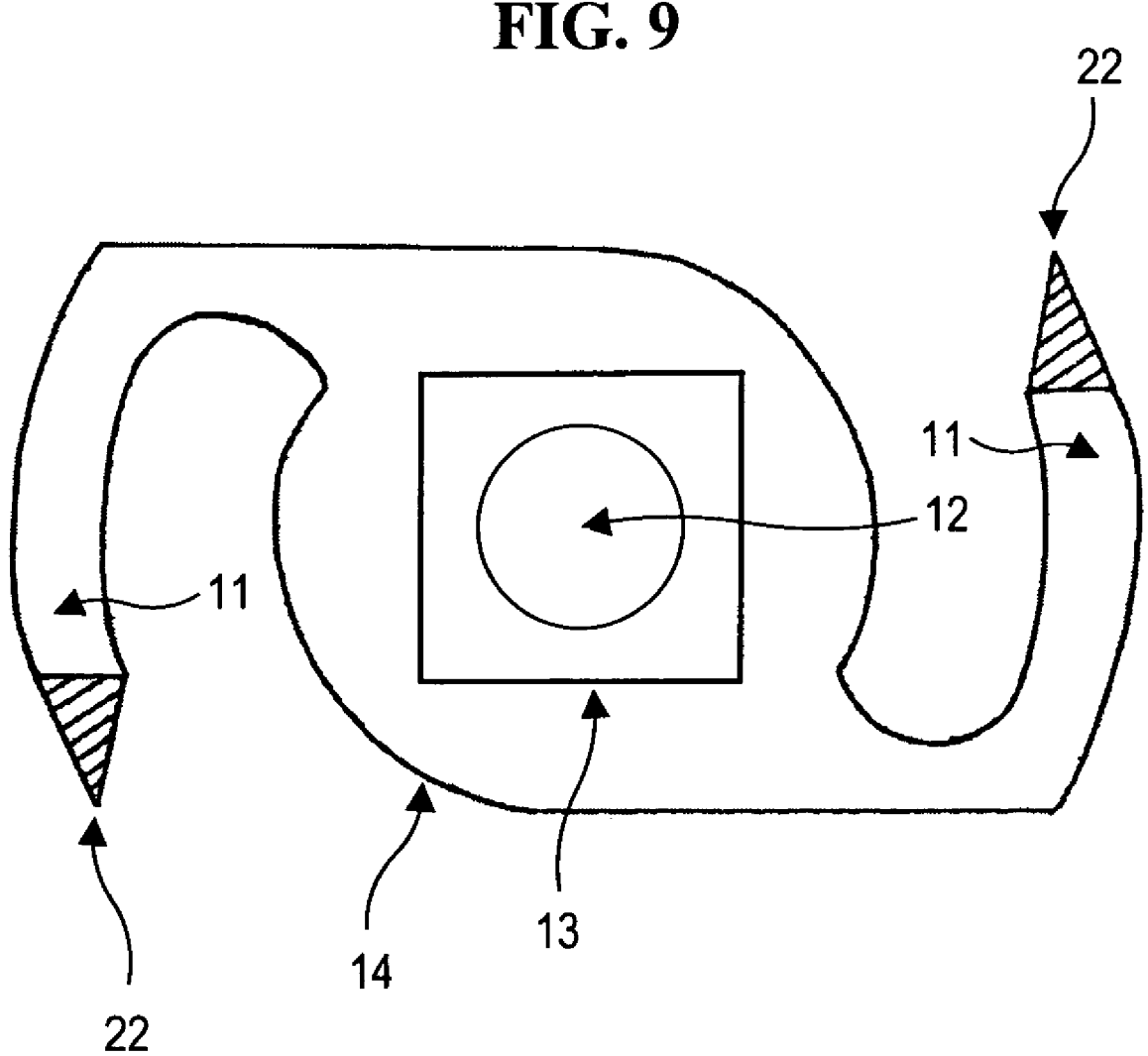
FIG. 9 Front view of the preferred embodiment of the counterclockwise blade.
Figure 10:
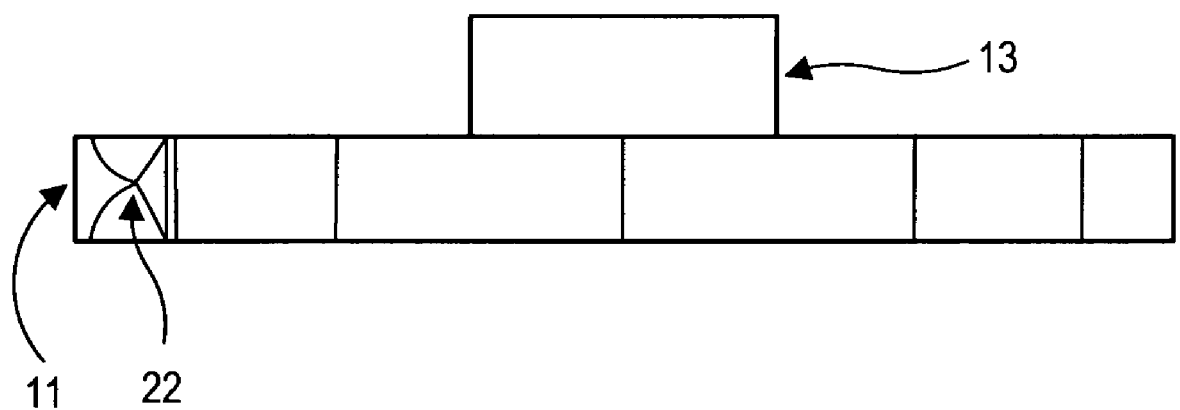
FIG. 10 Top view of the counterclockwise blade showing cutting extension (11) having sharp end (22) and control nut 13.

Once all the blades are engaged, a tightening nut is threaded onto the end of the shaft of FIG. 7.

Figure 18:
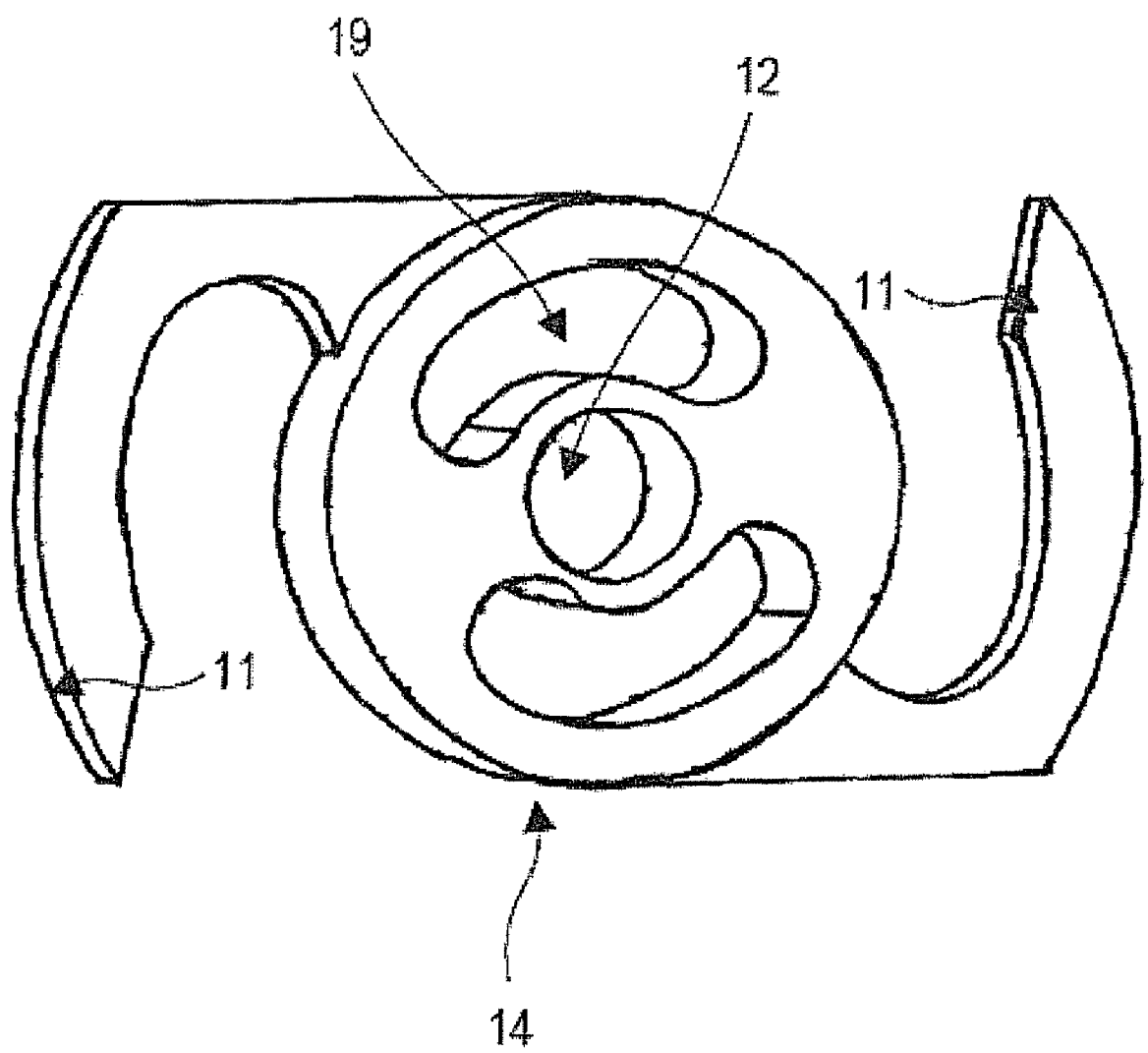
FIG. 18 Alternative embodiment of the blade having central opening (12) and control openings (19) on opposing sides of the central opening (12) to rotate the blade about the shaft (10). These blades are preloaded into the housing prior to placement of the housing into the disk space.
Figure 19:
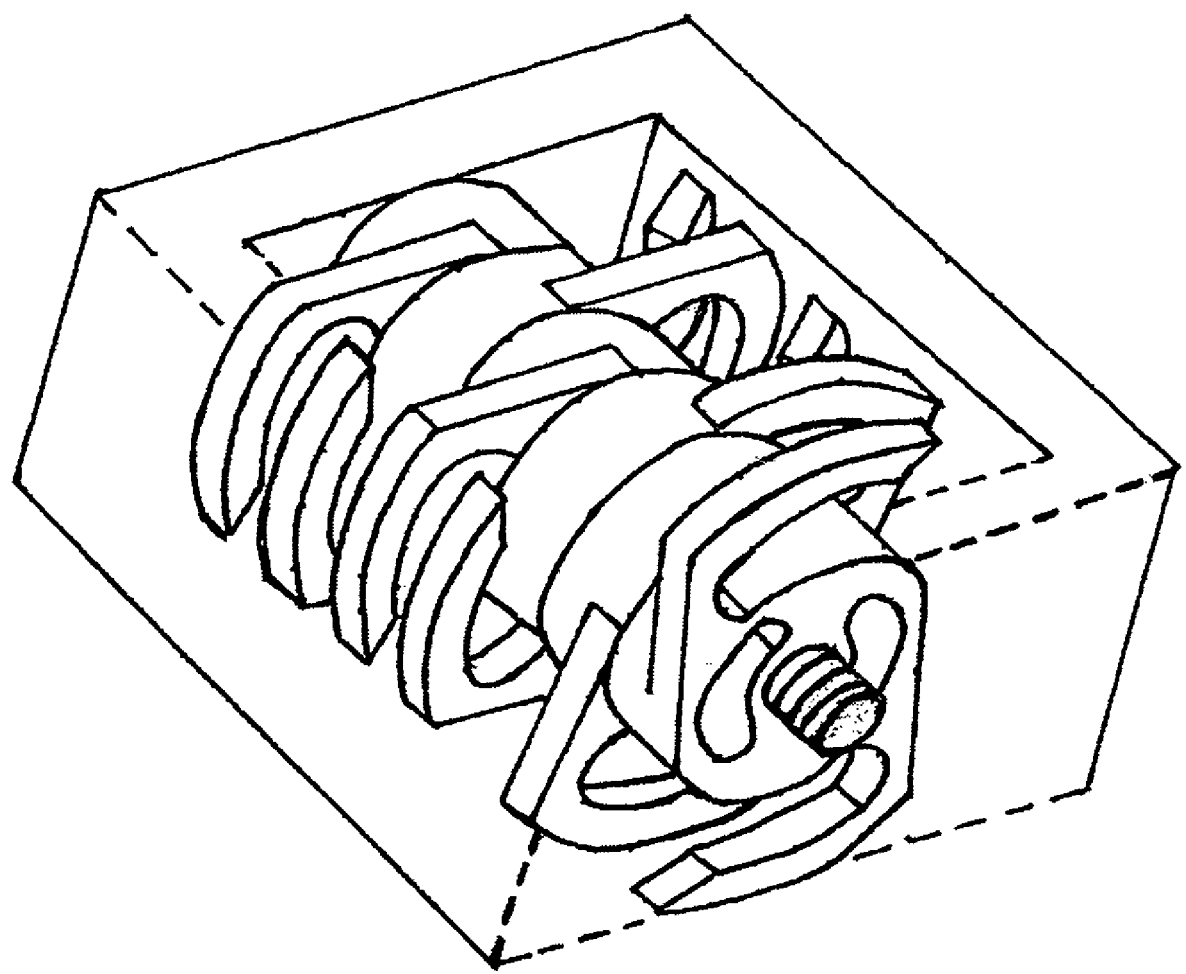
FIG. 19 Transparent housing and central shaft (10) with pre-loaded blades showing front two blades rotated into final vertical position.
Figure 20:
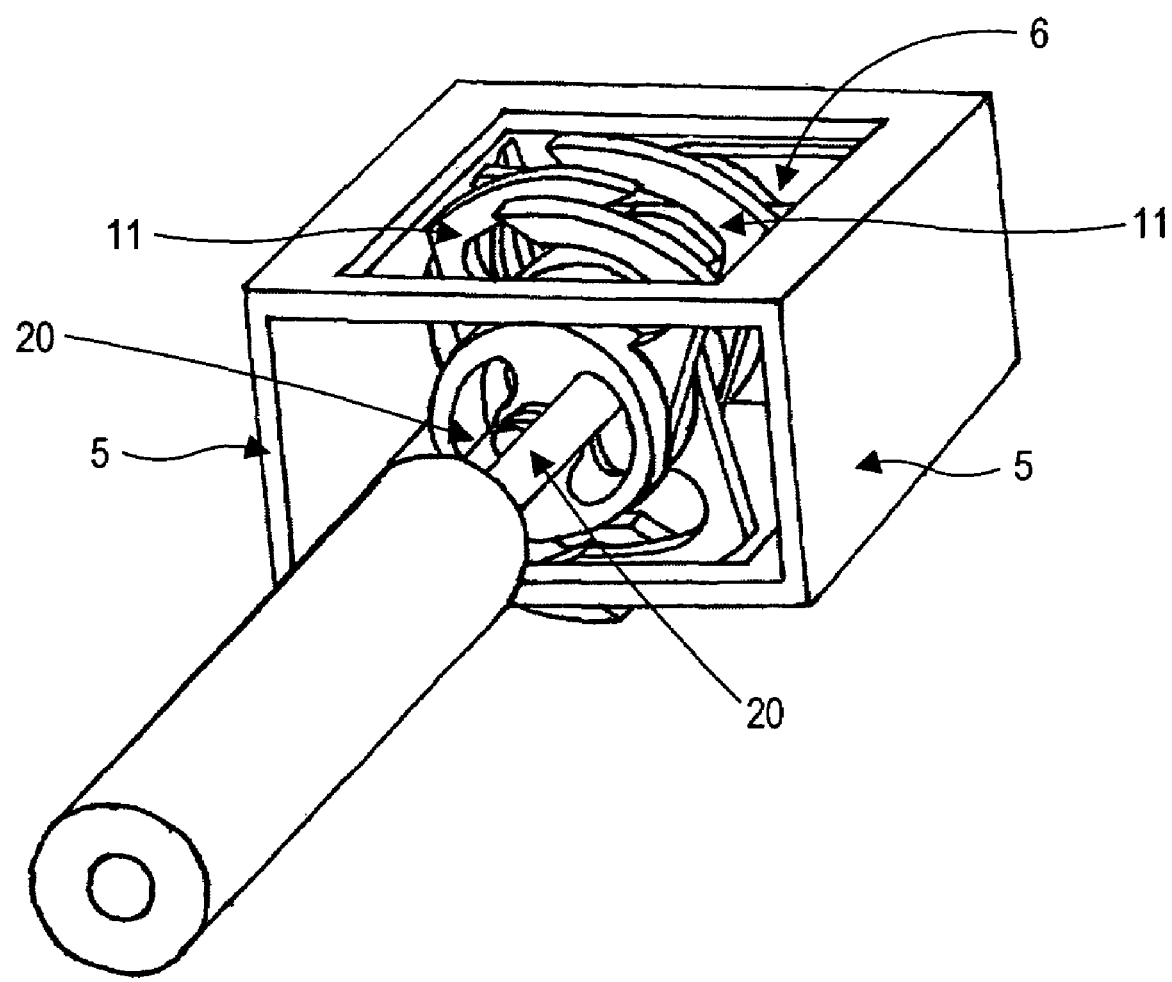
FIG. 20 Blade rotating tool fits into control openings (19) of clockwise and counterclockwise blades with prongs (20) of the rotating tool engaging the first three blades via control openings (19).

In an alternative embodiment alternating clockwise and counterclockwise blades (FIG. 18) are pre-loaded onto the shaft and inside the housing (FIG. 19). With the help of an introducer (FIG. 20) the blades are rotated sequentially going from the superficial to the deep.

In another embodiment the housing expands horizontally and contains two shafts, which separate from each other upon expansion of the housing. In the initial collapsed configuration, pre-loaded clockwise and counterclockwise blades threaded on different shafts imbricate between each other. After the cage is expanded, blades are pulled apart.

In another embodiment body of the blade is configured as an oval (FIGS. 8, 9, 11, 17) so that the disk space is expanded as a blade is rotated FIG. 17.

The invention claimed is:

1. A device utilized in reconstruction and fusion of a human spine providing direct rigid fixation of an anterior spinal column in flexion, extension and rotation, the device comprising:
 a housing including a leading deep surface conforming to a posterior aspect of an intervertebral disk and a trailing outer surface conforming to an anterior surface of the intervertebral disk, weight bearing sides and top and bottom surfaces with a plurality of openings enabling ingrowths of bone;
 a shaft running from a center of the leading deep surface and perpendicular to the leading deep surface of the housing to the center of the trailing outer surface of the housing, the shaft being affixed at least to the leading deep surface of the housing; and
 a plurality of fixation members individually disposed on the shaft of the housing, the plurality of fixation members including at least one first fixation member having at least one extension in a first orientation about the axis of the shaft and at least one second fixation member having at least one extension in a second orientation about the axis of the shaft that is opposite to the first orientation, wherein upon rotation of each fixation member of the plurality of fixation members about the axis of the shaft in a direction in which the at least one extension of each fixation member is oriented, the at least one extension of each fixation member is configured to break an endplate of a vertebra, hook into the vertebra, and rigidly secure the vertebra to the device to prevent separation of the vertebra from the device during spinal motion.

2. The device of claim 1, wherein the housing is configured in a shape of a box, a cylinder or other geometric shape including a configuration with a height of the leading deep surface smaller than a height of the trailing outer surface, the shape substantially conforming to a shape of a spinal disk space.

3. The device of claim 2, wherein the housing is expandable at least in part in vertical and horizontal directions to a tapered configuration.

4. The device of claim 2, wherein the housing comprises at least one material of metal, plastic, ceramic, graphite, coral and human bone products.

5. The device of claim 2, wherein the housing is absorbable.

6. The device of claim 2, wherein the housing is formed at least in part of a porous material.

7. The device of claim 2, wherein the plurality of fixation members vary in size to accommodate the configuration of the housing.

8. The device of claim 7, further comprising a means for individually introducing each fixation member of the plurality of fixation members into the housing and onto the shaft and for rotating each fixation member of the plurality of fixation members from horizontal orientation into vertical orientation.

9. The device of claim 7, further comprising a means for locking the plurality of fixation members in a final engaged position to prevent separation of the plurality of fixation members from the vertebra.

10. The device of claim 1, further comprising a plurality of shafts that serve as axis of rotation to the plurality of fixation members, the plurality of shafts are fixed or move away from each other when the housing is expanded at least in part in vertical and horizontal directions to a tapered configuration.

11. The device of claim 1, further comprising a means for rotating individually or as a group the plurality of fixation members that are pre-loaded onto the shaft of the housing.

12. The device of claim 1, wherein each fixation member of the plurality of fixation members includes two opposing extensions with sharp leading edges which are configured to hook into adjacent vertebrae to rigidly secure the adjacent vertebrae in relation to each other and to the device to prevent separation of the vertebrae from the device during spinal motion.

13. The device of claim 1, wherein the plurality of fixation members alternate between the first orientation and the second orientation of the at least one extension of each fixation member about the axis of the shaft.

14. The device of claim 1, wherein each fixation member of the plurality of fixation members includes a central portion having a shape configured to provide weight bearing support to the secured vertebra through at least one opening of the top and bottom surfaces.

15. The device of claim 1, wherein each fixation member of the plurality of fixation members comprises a central opening configured to allow each fixation member to be disposed on the shaft.

16. The device of claim 15, wherein each fixation member of the plurality of fixation members further comprises a control device disposed atop the central opening of each fixation member, the control device including a central opening to allow each fixation member to be disposed on the shaft, the control device further including a perimeter configured to facilitate introduction of each fixation member onto the shaft and rotation of each fixation member about the axis of the shaft.

17. The device of claim 16, wherein the control device is a control nut.

* * * * *